US00PP34564P2

(12) United States Plant Patent
Graff

(10) Patent No.: US PP34,564 P2
(45) Date of Patent: Sep. 13, 2022

(54) ***MANDEVILLA* PLANT NAMED 'QD20'**

(50) Latin Name: *Mandevilla sanderi*
Varietal Denomination: QD20

(71) Applicant: Poul Graff, Sabro (DK)

(72) Inventor: Poul Graff, Sabro (DK)

(73) Assignee: GRAFF BREEDING A/S, Sabro (DK)

( * ) Notice: Subject to any disclaimer, the term of this patent is extended or adjusted under 35 U.S.C. 154(b) by 0 days.

(21) Appl. No.: 17/694,099

(22) Filed: Mar. 14, 2022

(51) Int. Cl.
*A01H 6/08* (2018.01)
*A01H 5/02* (2018.01)

(52) U.S. Cl.
USPC ..... Plt./232

(58) Field of Classification Search
USPC ..... Plt./232
See application file for complete search history.

*Primary Examiner* — Annette H Para
(74) *Attorney, Agent, or Firm* — C. Anne Whealy

(57) ABSTRACT

A new and distinct cultivar of *Mandevilla* plant named 'QD20', characterized by its compact and broadly upright plant habit; moderately vigorous growth habit; freely branching habit; dense and bushy appearance; dark green-colored leaves; freely flowering habit; and relatively large strong red-colored flowers with orangish red-colored throats that are held upright above the foliar plane.

1 Drawing Sheet

Botanical designation: *Mandevilla sanderi.*
Cultivar denomination: 'QD20'.

STATEMENT REGARDING PRIOR DISCLOSURES BY INVENTOR/APPLICANT & ASSIGNEE

An European Community Plant Breeder's Rights application for the instant plant was filed by the Applicant/Assignee of the instant application, Graff Breeding A/S of Sabro, Denmark on Nov. 26, 2021, application number 2021/3053. Foreign priority is not claimed to this European Plant Breeder's Rights application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Mandevilla* plant, botanically known as *Mandevilla sanderi* and hereinafter referred to by the name 'QD20'.

The new *Mandevilla* plant is a product of a planned breeding program conducted by the Inventor in Sabro, Denmark. The objective of the breeding program is to create new compact and freely branching *Mandevilla* plants with numerous attractive flowers.

The new *Mandevilla* plant originated from a cross-pollination conducted by the Inventor in Sabro, Denmark in August, 2016 of a proprietary selection of *Mandevilla sanderi* identified as code number QD-0902, not patented, as the female, or seed, parent with a proprietary selection of

*Mandevilla sanderi* identified as code number QD-0442, not patented, as the male, or pollen, parent. The new *Mandevilla* plant was discovered and selected by the Inventor as a single flowering plant from within the progeny of the stated cross-pollination in a controlled greenhouse environment in Sabro, Denmark in May, 2017.

Asexual reproduction of the new *Mandevilla* plant by cuttings in a controlled greenhouse environment in Sabro, Denmark, since September, 2019 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'QD20'. These characteristics in combination distinguish 'QD20' as a new and distinct *Mandevilla* plant:

1. Compact and broadly upright plant habit.
2. Moderately vigorous growth habit.
3. Freely branching habit; dense and bushy appearance.
4. Dark green-colored leaves.
5. Freely flowering habit.
6. Relatively large strong red-colored flowers with reddish orange-colored throats that are held upright above the foliar plane.

Plants of the new *Mandevilla* can be compared to plants of the female parent selection. Plants of the new *Mandevilla* differ primarily from plants of the female parent selection in flower color as plants of the new *Mandevilla* have strong red-colored flowers whereas plants of the female parent selection have soft pink-colored flowers.

Plants of the new *Mandevilla* can be compared to plants of the male parent selection. Plants of the new *Mandevilla* differ primarily from plants of the male parent selection in leaf size as plants of the new *Mandevilla* have smaller leaves than plants of the male parent selection.

Plants of the new *Mandevilla* can also be compared to plants of *Mandevilla hybrida* 'Sunmanderemi', disclosed in U.S. Plant Pat. No. 16,449. In side-by-side comparisons, plants of the new *Mandevilla* differ primarily from plants 'Sunmanderemi' in the following characteristics:

1. Plants of the new *Mandevilla* are more compact than and not as vigorous as plants of 'Sunmanderemi'.
2. Plants of the new *Mandevilla* do not produce tendrils whereas plants of 'Sunmanderemi' produce tendrils.
3. Plants of the new *Mandevilla* have more rounded flowers than plants of 'Sunmanderemi'.

BRIEF DESCRIPTION OF THE PHOTOGRAPH

The accompanying colored photograph illustrates the overall appearance of the new *Mandevilla* plant showing the colors as true as it is reasonably possible to obtain in colored reproductions of this type. Colors in the photograph may differ slightly from the color values cited in the detailed botanical description which accurately describe the actual colors of the new *Mandevilla* plant. The photograph is a side perspective view of a typical flowering plant of 'QD20' grown in a container.

DETAILED BOTANICAL DESCRIPTION

The aforementioned photograph and following observations, measurements and values describe plants grown during the spring in 13-cm containers in a glass-covered greenhouse in Sabro, Denmark and under cultural practices typical of commercial *Mandevilla* production. During the production of the plants, day temperatures ranged from 20° C. to 25° C., night temperatures ranged from 19° C. to 21° C. and light levels ranged from 40 klux to 50 klux. Plants were pinched two times and were 31 weeks old when the photograph and description were taken. In the following description, color references are made to The Royal Horticultural Society Colour Chart, 2001 Edition, except where general terms of ordinary dictionary significance are used.

Botanical classification: *Mandevilla sanderi* 'QD20'.

Parentage:

*Female, or seed, parent*.—Proprietary selection of *Mandevilla sanderi* identified as code number QD-0902, not patented.

*Male, or pollen, parent*.—Proprietary selection of *Mandevilla sanderi* identified as code number QD-0442, not patented.

Propagation:

*Type*.—By vegetative cuttings.

*Time to initiate roots, summer and winter*.—About four weeks at soil and ambient temperatures about 21° C.

*Time to produce a rooted young plant, summer*.—About six weeks at soil and ambient temperatures about 21° C.

*Time to produce a rooted young plant, winter*.—About seven weeks at soil and ambient temperatures about 21° C.

*Root description*.—Fine, fleshy; typically close to 161C in color, actual color of the roots is dependent on substrate composition, water quality, fertilizers, substrate temperature and physiological age of roots.

*Rooting habit*.—Freely branching; dense.

*Tubers*.—Tuber formation has been observed on plants older than one year. Length: About 3 cm to 6 cm. Diameter: About 5 mm to 10 mm. Shape: Linear. Texture: Rough, glabrous. Color: Epidermis: Close to 157C. Cortical tissue: Close to 161C.

Plant description:

*Plant and growth habit*.—Compact and broadly upright plant habit; overall plant shape is broadly obovate; moderately vigorous growth habit and moderate growth rate; freely branching habit; dense and bushy appearance.

*Plant height, soil level to top of foliar plane*.—About 20 cm to 30 cm.

*Plant height, soil level to top of floral plane*.—About 21 cm to 31 cm.

*Plant diameter (spread)*.—About 25 cm to 35 cm.

*Lateral branch description*.—Branching habit: Freely branching habit, about two to four primary lateral branches each with typically four to six secondary lateral branches developing per plant. Length: About 10 cm to 25 cm. Diameter: About 5 mm. Internode length: About 1 cm to 3 cm. Aspect: Mostly upright. Strength: Strong. Texture and luster: Smooth, glabrous; semi-glossy to matte; becoming woody with development. Color, developing: Close to 144A. Color, developed: Close to 138B; when woody, becoming closer to 199A to 199B.

Leaf description:

*Arrangement*.—Opposite, decussate; simple.

*Length*.—About 3 cm to 5 cm.

*Width*.—About 2 cm to 4 cm.

*Shape*.—Elliptic.

*Apex*.—Cuspidate.

*Base*.—Obtuse, rounded.

*Margin*.—Entire.

*Texture and luster, upper surface*.—Smooth, glabrous; coriaceous; not rugose; semi-glossy.

*Texture and luster, lower surface*.—Smooth, glabrous; coriaceous; not rugose; matte.

*Venation pattern*.—Pinnate.

*Color*.—Developing leaves, upper surface: Close to 139A. Developing leaves, lower surface: Close to 146B, occasionally tinged with close to 165A. Full expanded leaves, upper surface: Close to 131A; venation, close to 138A. Fully expanded leaves, lower surface: Close to 138A to 138B; venation, close to N134A.

*Petioles*.—Length: About 3 mm to 5 mm. Diameter: About 2 mm to 3 mm. Strength: Moderately strong to strong. Texture and luster, upper and lower surfaces: Smooth, glabrous; semi-glossy to matte. Color, upper surface: Close to 144A. Color, lower surface: Close to 145A and 144A.

Flower description:

*Flower type and flowering habit*.—Single salverform flowers arranged singly or in terminal or axillary racemes; flowers rounded star-shaped and face upright to outwardly; freely flowering habit with about three to six flower buds and about one to two open flowers per inflorescence; about 40 to 50 flowers develop during the flowering season.

*Natural flowering season*.—Plants flower continuously from spring into the autumn in Denmark; plants begin flowering about nine to twelve weeks after final pinch.

*Flower longevity on the plant*.—About 8 to 14 days; flowers persistent.

*Fragrance*.—None detected.

*Inflorescence height* (*before flowers open*).—About 3 cm to 7 cm.

*Inflorescence diameter* (*before flowers open*).—About 3 cm to 7 cm.

*Flower buds*.—Length: About 2 cm to 6 cm. Diameter: About 1 cm to 2 cm. Shape: Rhomboidal. Texture and luster: Smooth, glabrous; slightly glossy. Color: Close to 46A.

*Flowers*.—Appearance: Flared trumpet, petals fused and five-parted; petals imbricate. Diameter: About 8 cm to 10 cm. Depth (length): About 3 cm to 4 cm. Throat diameter: About 2 cm to 3 cm. Tube length: About 2 cm. Tube diameter: About 4 mm to 5 mm.

*Petals*.—Quantity and arrangement: Five petals arranged in a single whorl; proximally, petals are fused into a funnelform tube. Petal length: About 3 cm to 4 cm. Petal width: About 3 cm to 4 cm. Petal shape and appearance: Unequal spatulate to fan-shaped. Petal apex: Acuminate to mucronate. Petal margin: Entire; slightly undulate. Petal texture and luster, upper and lower surfaces: Smooth, glabrous; not rugose; moderately velvety; matte. Throat texture: Smooth, glabrous; moderately velvety. Tube texture: Smooth, glabrous; slightly velvety. Color: Petal, when opening, upper and lower surfaces: Close to 46A. Petal, fully opened, upper surface: Close to 46A; venation, close to 53A; color becoming closer to 46B with subsequent development. Petal, fully opened, lower surface: Close to 46A; venation, close to 157A; color becoming closer to 53B with subsequent development. Throat: Close to N172A; venation, close to 53A. Tube: Close to N144D; venation, close to N144D.

*Sepals*.—Quantity and arrangement: Five sepals arranged in a single whorl. Sepal length: About 5 mm to 10 mm. Sepal width: About 2 mm to 5 mm. Sepal shape: Lanceolate. Sepal apex: Acuminate. Sepal base: Rounded. Sepal margin: Entire. Sepal texture and luster, upper and lower surfaces: Smooth, glabrous; semi-glossy. Sepal color: When opening, upper and lower surfaces: Close to 145B; towards the apex, close to 46B and towards the base, close to 146B. Fully opened, upper and lower surfaces: Close to 145B; towards the apex, close to 46B and towards the base, close to 146B.

*Peduncles*.—Length: About 2 cm to 5 cm. Diameter: About 3 mm to 5 mm. Strength: Strong. Aspect: Mostly upright. Texture and luster: Smooth, glabrous; semi-glossy. Color: Close to 144A.

*Pedicels*.—Length: About 5 mm to 10 mm. Diameter: About 3 mm to 5 mm. Strength: Strong. Aspect: Mostly upright. Texture and luster: Smooth, glabrous; semi-glossy. Color: Close to 145A.

*Reproductive organs*.—Stamens: Quantity and arrangement: Typically five; basifixed; anthers connivent. Filament length: About 1 mm to 2 mm. Filament color: Close to 157C. Anther size: About 2 mm by 3 mm. Anther shape: Linear. Anther color: Close to 160C. Pollen amount: Moderate. Pollen color: Close to 162C. Pistils: Quantity: Typically two. Pistil length: About 2 cm. Style length: About 1 cm to 2 cm. Style color: Close to 157B. Stigma diameter: About 3 mm to 4 mm. Stigma shape: Rounded to deltoid. Stigma color: Close to 138B. Ovary color: Close to 160C

*Fruits*.—Quantity per flower: One. Length: About 10 cm to 20 cm. Diameter: About 2 mm to 5 mm. Texture: Smooth, glabrous. Color: Close to 138A.

*Seeds*.—Quantity per fruit: More than 100. Length: About 5 mm to 10 mm. Diameter: About 0.5 mm. Texture: Smooth, glabrous. Color: Close to 200D.

Pathogen & pest resistance: To date, plants of the new *Mandevilla* have not been noted to be resistant to pathogens and pests common to *Mandevilla* plants.

Temperature tolerance: Plants of the new *Mandevilla* have been observed to tolerate temperatures of about 10° C. to 44° C. and to be suitable for USDA Hardiness Zones 10B through 13.

It is claimed:

1. A new and distinct *Mandevilla* plant named 'QD20' as illustrated and described.

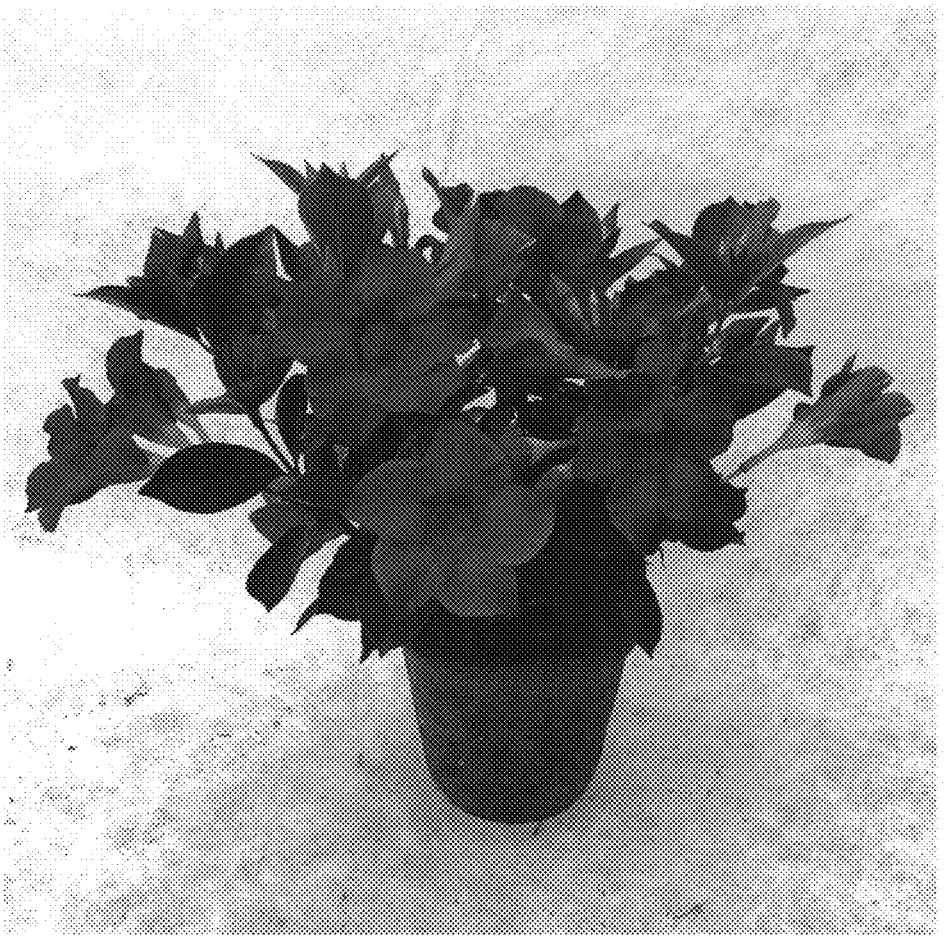

* * * * *